US012290312B2

United States Patent
Bacher et al.

(10) Patent No.: US 12,290,312 B2
(45) Date of Patent: May 6, 2025

(54) MEASUREMENT OF PULSED LASER OUTPUT USING OPTICAL DETECTION OF DUTY CYCLE

(71) Applicant: Alcon Inc., Fribourg (CH)

(72) Inventors: Gerald David Bacher, Carlsbad, CA (US); Derek Chen, Irvine, CA (US); Conrad Sawicz, Tustin, CA (US); Dan Teodorescu, Irvine, CA (US)

(73) Assignee: Alcon Inc., Fribourg (CH)

( * ) Notice: Subject to any disclaimer, the term of this patent is extended or adjusted under 35 U.S.C. 154(b) by 267 days.

(21) Appl. No.: 17/083,707

(22) Filed: Oct. 29, 2020

(65) Prior Publication Data

US 2021/0135424 A1    May 6, 2021

Related U.S. Application Data

(60) Provisional application No. 62/930,263, filed on Nov. 4, 2019.

(51) Int. Cl.
    *H01S 3/13*      (2006.01)
    *A61B 18/20*      (2006.01)
    *H01S 3/0941*      (2006.01)

(52) U.S. Cl.
CPC ............ *A61B 18/20* (2013.01); *H01S 3/0941* (2013.01); *H01S 3/1305* (2013.01); *H01S 3/1306* (2013.01)

(58) Field of Classification Search
None
See application file for complete search history.

(56) References Cited

U.S. PATENT DOCUMENTS

| 5,071,249 A | 12/1991 | Takahashi et al. |
| 5,982,790 A * | 11/1999 | Grossman ................. H01S 3/13 |
| | | 372/30 |

(Continued)

FOREIGN PATENT DOCUMENTS

| EP | 3147694 A1 | 3/2017 |
| EP | 3260890 A1 | 12/2017 |

(Continued)

OTHER PUBLICATIONS

"Area under a curve by Integration", Interactive Mathematics; Aug. 4, 2017, https://web.archive.org/web/20170804195139/http://www.intmath.com/applications-integration/2-area-under-curve.php (Year: 2017).*

*Primary Examiner* — Tod T Van Roy
(74) *Attorney, Agent, or Firm* — PATTERSON + SHERIDAN, LLP

(57) ABSTRACT

Systems and methods are disclosed for measuring pulsed laser output. An example system comprises a laser configured to emit output in pulses; at least one sensor positioned to sense laser output and configured to convert that output into electrical signals; an edge detector configured to detect at least leading edges of a plurality of laser pulses; an analog to digital converter configured to convert electrical signals from a sensor into digital signals indicative of laser power output; and a controller; wherein, based on the detection of at least the leading edges of the laser pulses, the controller is configured to obtain samples of laser power output during each of the laser pulses. The system may use the samples of laser power output in a feedback loop to automatically adjust laser power.

17 Claims, 2 Drawing Sheets

(56) References Cited

U.S. PATENT DOCUMENTS

| | | | |
|---|---|---|---|
| 7,020,169 B2* | 3/2006 | Nishimura | H01S 5/06832 |
| | | | 347/237 |
| 7,876,794 B2* | 1/2011 | Kakui | H01M 8/04186 |
| | | | 372/71 |
| 8,693,514 B2* | 4/2014 | Tamaoki | H01S 5/06216 |
| | | | 372/25 |
| 8,786,942 B2* | 7/2014 | Palese | H01S 3/1301 |
| | | | 359/341.1 |
| 8,801,193 B2* | 8/2014 | Chihara | H04N 9/3129 |
| | | | 372/38.01 |
| 9,641,259 B1* | 5/2017 | Charlantini | H04B 10/40 |
| 10,054,711 B2* | 8/2018 | Ferchau | G01V 8/20 |
| 10,096,969 B1* | 10/2018 | Aggarwal | G03F 7/70025 |
| 10,122,473 B2* | 11/2018 | Charlantini | H04B 10/50 |
| 2002/0009115 A1* | 1/2002 | Sumiyoshi | G02F 1/39 |
| | | | 372/75 |
| 2002/0154669 A1* | 10/2002 | Spangler | G03F 7/70041 |
| | | | 372/55 |
| 2003/0198262 A1* | 10/2003 | Tanner | H01S 5/06216 |
| | | | 372/25 |
| 2014/0218791 A1* | 8/2014 | Desbiens | H01S 3/1001 |
| | | | 359/345 |
| 2015/0372761 A1* | 12/2015 | Boutaud | H04B 10/516 |
| | | | 398/140 |
| 2016/0058493 A1* | 3/2016 | Neal, II | A61B 18/1233 |
| | | | 606/34 |
| 2017/0090065 A1* | 3/2017 | Ferchau | G01V 8/20 |
| 2018/0106963 A1* | 4/2018 | Otani | H01S 3/10 |
| 2018/0159290 A1* | 6/2018 | Hunter, Jr. | H01S 3/0092 |
| 2019/0089120 A1* | 3/2019 | Abeeluck | H01S 3/0941 |

FOREIGN PATENT DOCUMENTS

| | | |
|---|---|---|
| JP | H0391938 U | 9/1991 |
| JP | H09162931 A | 6/1997 |
| JP | 2006-80896 A | 3/2006 |
| JP | 2013545094 A | 12/2013 |

* cited by examiner

MEASUREMENT OF PULSED LASER OUTPUT USING OPTICAL DETECTION OF DUTY CYCLE

TECHNICAL FIELD

The present disclosure is directed to measurement of the output of a pulsed laser, such as a pulsed laser used in ophthalmic procedures.

BACKGROUND

Lasers are used in many different medical procedures including a number of different ophthalmic procedures. For example, therapeutic lasers are used for photocoagulation of retinal tissue to treat issues such as retinal tears and the effects of diabetic retinopathy. In an example of such procedures, the distal end of a laser probe is introduced into the eye globe through a trocar cannula. The laser system can be activated to emit a low power aiming laser beam, which may be a first color such as red, to show where the laser probe is pointed. When the operator (e.g., an eye surgeon) has the aiming laser beam pointed at the intended spot, the operator then can activate the laser system to emit a therapeutic laser beam, which may be a second color such as green, to the intended spot, or areas around the intended spot, to effect treatment (e.g., photocoagulation).

For some laser applications, it can be desirable to use a pulsed laser. In a pulsed laser, the laser output occurs in a series of short pulses, rather than in a continuous wave. Pulsed lasers can be useful for therapeutic lasers, such as those used in ophthalmic procedures, e.g., for photocoagulation of retinal tissue.

In laser systems, it is often desirable to determine the power or energy output of the laser in order to ascertain whether the desired amount of output is being effectuated and to adjust the laser output accordingly. In some systems, laser output has been determined based upon the electrical signal that is used to drive the laser. However, the visible output of the laser may not directly follow the supplied current. This drawback may be exacerbated in certain types of lasers. For example, when turning on and off the output of an intracavity doubled diode pumped solid state (DPSS) laser by modulating the current supplied to the pump laser diode, due to the physics of the various processes used to generate the laser output, the output may lag the supplied current on the leading edge and the trailing edge. This makes the duty cycle of the laser difficult to measure directly from the electrical signal. In addition, artifacts such as leading edge overshoot and various other oscillations can occur during the laser output, further causing the laser output to be difficult to measure directly from the electrical signal.

In other systems, laser output has been determined by using a sensor such as a photodiode to continuously sample and thereby continuously monitor the laser output. This method can require very high sample rates, which can require high bandwidth electronics and processing, thereby complicating processing requirements.

There is a need for improved systems and methods for measuring the output of a pulsed laser, such as a pulsed laser used in ophthalmic procedures.

SUMMARY

The present disclosure is directed to improved systems and methods for measuring the output of a pulsed laser, such as a pulsed laser used in ophthalmic procedures.

In some embodiments, a system for measuring pulsed laser output comprises a laser configured to emit output in pulses; at least one sensor positioned to sense output from the laser and configured to convert that output into electrical signals; an edge detector configured to receive electrical signals from the at least one sensor and to detect from those electrical signals at least leading edges of a plurality of pulses from the laser; an analog to digital converter configured to receive electrical signals from the at least one sensor and to convert those electrical signals into digital signals indicative of laser power output; and a controller; wherein, based on the detection by the edge detector of at least the leading edges of the plurality of pulses from the laser, the controller is configured to obtain from the analog to digital converter a plurality of samples of laser power output during the plurality of pulses from the laser.

In some embodiments, the edge detector may be configured to detect the leading edges and trailing edges of the plurality of pulses from the laser. The controller may be configured to obtain from the analog to digital converter the plurality of samples of laser power output during the plurality of pulses from the laser based on the detection by the edge detector of the leading edges and the trailing edges of the plurality of pulses from the laser.

In some embodiments, the controller may be configured to refrain from sampling laser power output between pulses from the laser. In some embodiments, the controller may be configured to sample laser power output between pulses from the laser at a reduced sample rate between pulses as compared to a sample rate of laser power output during pulses.

In some embodiments, the system may be configured to use the plurality of samples of laser power output during the plurality of pulses from the laser in a feedback loop to automatically adjust laser power to a desired level.

In some embodiments, the laser is configured to emit output in pulses ranging in duration from 1 microsecond to 100 microseconds. In some embodiments, the laser is an intracavity doubled diode pumped solid state laser.

In some embodiments, the at least one sensor positioned to sense output from the laser and configured to convert that output into electrical signals comprises a first sensor configured to send electrical signals at least to the edge detector and a second sensor configured to send electrical signals at least to the analog to digital converter. In some embodiments, the at least one sensor positioned to sense output from the laser and configured to convert that output into electrical signals comprises a single sensor configured to send electrical signals to the edge detector and to the analog to digital converter. In some embodiments, the at least one sensor positioned to sense output from the laser and configured to convert that output into electrical signals comprises at least one photodiode sensor.

In some embodiments, the system further comprises a driver that is configured to drive the laser and that is configured to be controlled by the controller. In some embodiments, the system further comprises a sync timer configured to enable keeping track of time between one or more components of the system.

In some embodiments, a method of measuring pulsed laser output comprises operating a laser to emit output in pulses; sensing the output from the laser and converting that output to electrical signals; detecting from the electrical signals the leading edges of a plurality of pulses from the laser; and, based at least on the detection of the leading edges of the plurality of pulses, obtaining a plurality of samples of laser power output during the plurality of pulses from the laser.

In some embodiments, the method may further comprise detecting from the electrical signals the trailing edges of the plurality of pulses from the laser. In some embodiments, the step of obtaining the plurality of samples of laser power output during the plurality of pulses from the laser is performed based the detection of the leading edges and the trailing edges of the plurality of pulses.

In some embodiments, the step of obtaining a plurality of samples of laser power output during the plurality of pulses from the laser is performed at a first sample rate, and the method further comprises obtaining one or more samples of laser power output between pulses from the laser at a second sample rate, wherein the second sample rate is lower than the first sample rate. In some embodiments, the method further comprises refraining from sampling laser power output between pulses from the laser.

In some embodiments, the method further comprises using the plurality of samples of laser power output during the plurality of pulses from the laser in a feedback loop to automatically adjust laser power to a desired level.

These and other embodiments and their advantages will be appreciated and understood by persons of ordinary skill in the art in view of the description herein and the accompanying drawings.

BRIEF DESCRIPTION OF THE DRAWINGS

The accompanying drawings illustrate example implementations of the devices and methods disclosed herein and, together with the description, serve to explain the principles of the present disclosure.

Figure 1:
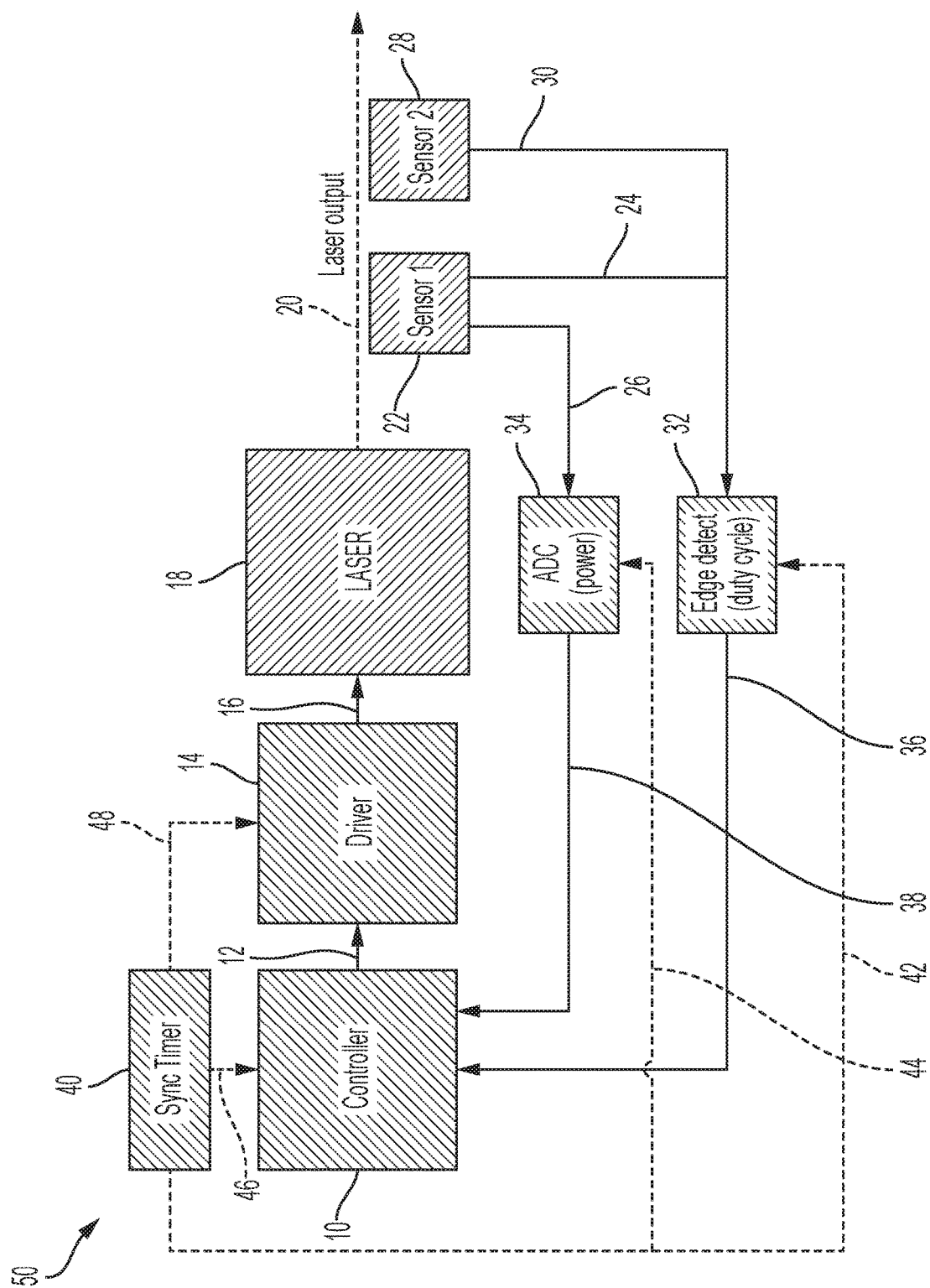
FIG. 1 shows a schematic diagram of an example system for measuring the output of a pulsed laser.

The accompanying drawings may be better understood by reference to the following detailed description.

DETAILED DESCRIPTION

For the purposes of promoting an understanding of the principles of the disclosure, reference will now be made to the implementations illustrated in the drawings, and specific language will be used to describe the same. It will nevertheless be understood that no limitation of the scope of the disclosure is intended. Any alterations and further modifications to the described systems, devices, instruments, or methods, and any further application of the principles of the present disclosure, are fully contemplated as would normally occur to one skilled in the art to which the disclosure relates. In particular, the features, components, and/or steps described with respect to one implementation may be combined with the features, components, and/or steps described with respect to other implementations of the disclosure. For simplicity, in some instances the same reference numbers are used throughout the drawings to refer to the same or like parts.

FIG. 1 shows a schematic diagram of an example system 50 for measuring the output of a pulsed laser. A system for measuring the output of a pulsed laser such as the system 50 in FIG. 1 may be implemented in a laser system for ophthalmic procedures, such as photocoagulation of retinal tissue. The system 50 may be implemented as part of an overall laser system that may be a stand-alone laser system or a laser module for an ophthalmic system used for ophthalmic procedures. For example, a system for measuring the output of a pulsed laser such as the system 50 in FIG. 1 may be incorporated into a laser system similar to the PUREPOINT® Vision System of Alcon, headquartered in Fort Worth, Texas, which may be used as a stand-alone laser system or as a laser module for a control console like the control console of the CENTURION® Vision System, also of Alcon.

The example system 50 shown in FIG. 1 includes a laser 18 that may be operated as a pulsed laser, i.e., it may be operated such that the laser output occurs in a series of short pulses, rather than in a continuous wave. As one example, the laser 18 may be an intracavity doubled diode pumped solid state (DPSS) laser operated as a pulsed laser by modulating the current supplied to the pump laser diode. The laser 18 in this example emits output that is useful for photocoagulation of retinal tissue in an ophthalmic procedure. The emitted output may be, for example, visible light in the green spectral range, for example in the range of 520 nm to 560 nm. As one example, the emitted output from laser 18 may be green visible light having a wavelength at or around 532 nm. Other types of lasers and laser outputs of different wavelengths may be used.

In some embodiments, the pulsing of the laser 18 may occur in short pulses wherein each pulse is in the range of 1 to 100 microseconds or less. In other embodiments, the pulsing of the laser 18 may occur in longer pulses wherein each pulse is longer than 100 microseconds, for example in the range of 100 microseconds to 30 milliseconds, or greater than 30 milliseconds. In some applications, the operation of the laser with short pulses may have a therapeutic or clinical benefit.

The laser 18 may be operated by a controller 10 that controls a driver 14 that drives the laser 18. The controller 10 communicates with the driver 14 as indicated by communication path 12. The driver 14 communicates with the laser 18 as indicated by communication path 16.

FIG. 1 shows the laser output 20, which is emitted from laser 18 in a series of short pulses. As shown in FIG. 1, the system 50 includes one or more sensors, such as a first sensor 22 and a second sensor 28. In some embodiments, the system 50 may include only a first sensor 22, and the second sensor 28 may be omitted.

Each sensor, such as first sensor 22 and second sensor 28 (if used) is a sensor capable of measuring the output of the laser 18. For example, each of the sensors 22, 28 may be a suitable optical sensor such as a semiconductor photodiode sensor that converts light into an electrical signal. For example, each of the sensors 22, 28 may be a semiconductor photodiode sensor that generates an electrical signal proportional to the laser power. The conversion of the electrical signal to laser power can be calibrated when the system 50 is manufactured, so that the sensor(s) can provide an output reflective of the sensed laser power.

In some embodiments, in order to direct light from the laser 18 to the first sensor 22 and second sensor 28 (if used), a beam splitter (not shown) may be placed in the output path to direct a fraction of the laser output to the sensor. For example, a first beam splitter may be used to direct around one percent or less of the laser output to first sensor 22, and a second beam splitter may be used to direct around one percent or less of the laser output to second sensor 28 (if used), leaving the remaining laser output to be directed to the intended target.

In one example embodiment, the system 50 includes only a first sensor 22, and not a second sensor 28. In this example, the first sensor 22 provides output to an edge detector 32 and to an analog to digital converter (ADC) 34. The first sensor 22 communicates with the edge detector 32 as indicated by communication path 24. The first sensor 22 communicates with the analog to digital converter 34 as indicated by communication path 26.

In other example embodiments, the system 50 may include a first sensor 22 and a second sensor 28. In such examples, one of the first or second sensors 22, 28 provides output to an edge detector 32, and the other of the first or second sensors 22, 28 provides output to an analog to digital converter 34. For example, the first sensor 22 may provide output to the edge detector 32 along communication path 24, and the second sensor 28 may provide output to the analog to digital converter 34 along another communication path (not shown). In such an example, communication paths 26 and 30 as illustrated in FIG. 1 may be omitted. As another example, the second sensor 28 may provide output to the edge detector 32 along communication path 30, and the first sensor 22 may provide output to the analog to digital converter 34 along communication path 26. In such an example, communication path 24 as illustrated in FIG. 1 may be omitted. In another example, both the first and second sensors 22, 28 may communicate with and provide output to both the edge detector 32 and the analog to digital converter 34.

The designations "first" and "second" as used herein with respect to the sensors are not meant to indicate or imply any particular positioning or other characteristic of the sensors. Rather, when the designations "first" and "second" are used herein with respect to the sensors, they are used only to distinguish one sensor from the other. For example, the first sensor or the second sensor may be positioned closer to the laser output, the first sensor and/or the second sensor may provide output to the edge detector, and the first sensor and/or the second sensor may provide output to the analog to digital converter.

The edge detector 32 is a component that can detect an edge of a laser pulse from the signal received from the connected sensor. The laser output has a duty cycle representing that period of time during which the laser is emitting electromagnetic radiation (e.g., light). The edge detector 32 may include a comparator that compares the signal received from the connected sensor to a threshold amount. When the threshold is crossed, the comparator changes logic. For example, when the laser output turns on, i.e., begins a pulse, the signal from the sensor connected to the edge detector 32 goes from below the threshold to above the threshold, the comparator changes logic to indicate the presence of output or a high output, and the edge detector 32 detects the leading edge of the pulse. When the laser output turns off, i.e., ends a pulse, the signal from the sensor connected to the edge detector 32 goes from above the threshold to below the threshold, the comparator changes logic to indicate the lack of output or a low output, and the edge detector 32 detects the trailing edge of the pulse. The amount of the threshold can be adjusted to a desired amount based upon the application. The edge detector 32 can provide output to the controller 10 as indicated by communication path 36. In alternative embodiments, the edge detector 32 may be implemented as part of the controller 10.

The analog to digital converter 34 is a component that can convert the electrical signal received from the connected sensor into a digital signal representing or indicative of the laser power. The connected sensor may be continuously outputting to the analog to digital converter 34, so the analog to digital converter 34 can provide a reading to the controller 10 for any desired moment in time. The analog to digital converter can provide output to the controller 10 as indicated by communication path 38. In alternative embodiments, the analog to digital converter 34 may be implemented as part of the controller 10.

As shown in FIG. 1, the system 50 further includes a sync timer 40 that enables keeping track of time between one or more of the components of the system 50. As shown in FIG. 1, a signal may be communicated between the sync timer 40 and the edge detector 32 along communication path 42, a signal may be communicated between the sync timer 40 and the analog to digital converter 34 along communication path 44, a signal may be communicated between the sync timer 40 and the controller 10 along communication path 46, and/or a signal may be communicated between the sync timer 40 and the driver 14 along communication path 48.

In an example embodiment, the sync timer 40 provides common time information to one or more of the designated components. In this manner, for example, the controller 10 can associate a signal from the edge detector 32, such as the leading edge of a pulse or the trailing edge of a pulse, with a specific moment in time as kept by the sync timer 40. Similarly, the controller 10 can request sample readings from the analog to digital converter 34 at specific moments in time as kept by the sync timer 40, for example at certain periods of time after the edge detector 32 detects a leading edge of a pulse. Each component may have the capability to time stamp an event or signal based on the timing information from the sync timer 40.

Figure 2:
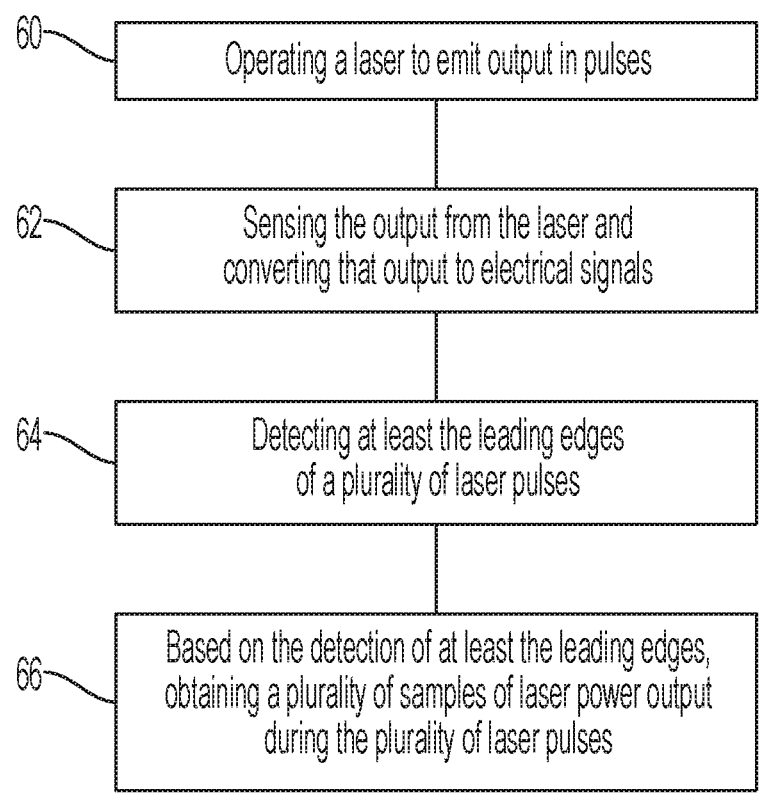
FIG. 2 shows a flow chart of an example method for measuring the output of a pulsed laser.

FIG. 2 shows a flow chart of an example method for measuring the output of a pulsed laser using the example system of FIG. 1. The example method steps shown in FIG. 2 represent only an embodiment, as other variations are possible within the scope of the disclosure.

In step 60, the controller 10 directs the driver 14 to operate the laser 18 such that the laser 18 emits pulsed output. The controller 10 may direct the driver 14 to operate the laser 18 in accordance with a desired instantaneous power level output of the laser 18 for a desired time interval.

In step 62, a sensor 22 and/or 28 senses the laser output, converts that laser output to electrical signals, and sends those electrical signals reflective of that output to the edge detector 32. In some embodiments, the sensor 22 and/or 28 continuously senses the laser output and continuously sends electrical signals reflective of that output to the edge detector 32.

In step 64, the edge detector 32 detects at least the leading edges of a plurality of laser pulses and sends signals indicating such detection to the controller 10. The signals may include the times of the leading edges of the laser pulses as indicated by the sync timer 40, and/or the controller 10 may record the times of the leading edges of the laser pulses as indicated by the sync timer 40.

In step 66, based on the detection of at least the leading edges, the controller 10 obtains a series of samples from the analog to digital converter 34 representative of laser power during the laser pulses, at specific moments in time as kept by the sync timer 40. For example, in an embodiment with a pulse length of 15 microseconds, the controller 10 may obtain 5 to 15 sample readings from the analog to digital converter 34 during each pulse. The controller 10 may obtain a plurality of sample readings from the analog to digital converter 34 during each pulse and may obtain such sample readings for a plurality of pulses. In one example, the controller 10 obtains the sample signals from the analog to digital converter 34 by sending one or more commands to the analog to digital converter 34 to perform, at specific times, a series of conversions of the analog signals from the associated sensor 22 or 28 to digital signals indicating laser power at those times. In some embodiments, the controller 10 may request the conversions from the analog to digital converter 34 based upon the times of the leading edges of pulses as indicated by the edge detector 32. For example, the controller 10 may request the conversions from the analog to digital converter 34 at certain numbers of timer cycles or timer increments from the times of the leading edges of the pulses.

In some embodiments, a method for measuring the output of a pulsed laser method may include other steps in addition to those shown in FIG. 2 or described above. For example, the edge detector 32 may also detect the trailing edges of the laser pulses and may send signals indicating such detections to the controller 10. The signals may include the times of the trailing edges of the laser pulses as indicated by the sync timer 40, and/or the controller 10 may record the times of the trailing edges of the laser pulses as indicated by the sync timer 40.

In some embodiments, the controller 10 may refrain from requesting conversions from the analog to digital converter 34 between pulses, i.e., the sample rate of laser power between pulses may be zero. In some embodiments, the controller 10 may request conversions from the analog to digital converter 34 at a significantly reduced sample rate between pulses as compared to the sample rate during pulses.

If desired, the controller 10 may obtain one or more signals from the analog to digital converter 34 representative of laser power during the period between pulses in order to confirm that the laser is not outputting during that time. The controller 10 may obtain a signal from the analog to digital converter 34 by sending a command to the analog to digital converter 34 to perform, at one or more specific times between pulses, one or more conversions of the analog signal from the associated sensor 22 or 28 to a digital signal indicating laser power at the desired time(s).

In some embodiments, the controller 10 may utilize the trailing edge information in order to refrain from requesting conversions from the analog to digital converter 34 until the next pulse, or in order to reduce the rate of conversions from the analog to digital converter 34 until the next pulse. In some embodiments, the controller 10 may utilize the leading edge information and a known or expected pulse duration in order to refrain from requesting conversions from the analog to digital converter 34 until the next pulse, or in order to reduce the rate of conversions from the analog to digital converter 34 until the next pulse.

Steps as described above, or a subset of such steps, may be repeated during operation of the laser in order to get continuous readings as the laser is operating. For example, the sensor 22 and/or 28 connected to the edge detector 32 may continuously detect the laser output and may continuously send signals reflective of that output to the edge detector 32. The edge detector 32 may detect the leading edges, or the leading and trailing edges, of each laser pulse in a plurality of laser pulses and may send signals indicating such detections to the controller 10. In some embodiments, the edge detector 32 may operate continuously to detect the leading edges, or the leading and trailing edges, of each laser pulse during operation and may send signals indicating such detections to the controller 10. As described above, the signals from the edge detector 32 may include the times of the leading edges, or the leading and trailing edges, of the laser pulses as indicated by the sync timer 40, and/or the controller 10 may record the times of the leading edges, or the leading and trailing edges, of the laser pulses as indicated by the sync timer 40.

In addition, the sensor 22 and/or 28 connected to the analog to digital converter 34 may continuously detect the laser output and may continuously send signals reflective of that output to the analog to digital converter 34. For each pulse detected by the edge detector 32, the controller 10 may obtain a series of signals from the analog to digital converter 34 representative of laser power during that pulse, at specific moments in time as kept by the sync timer 40. As one example, the controller 10 may obtain 5 to 15 sample readings from the analog to digital converter 34 during each pulse.

In some embodiments, the system 50 may use the power readings in a feedback loop to automatically adjust the laser power to a desired level. For example, if the power readings are showing that the laser 18 is outputting less than the desired amount of power, the controller 10 may direct the driver 14 to operate the laser 18 at a higher power, for example by increasing the amount of current to the laser 18. Similarly, if the power readings are showing that the laser 18 is outputting more than the desired amount of power, the controller 10 may direct the driver 14 to operate the laser 18 at a lower power, for example by decreasing the amount of current to the laser 18. The adjustments may be made continuously or at intervals, for example every few pulses, or every millisecond or another time interval.

In some embodiments, the system 50 may use the power readings to output information to another system or to an operator of the system, for example on a display. For example, the system 50 may use the power readings to output information regarding the laser's power or energy.

In some embodiments, the system 50 may use the power readings to calculate a pulse energy. By measuring both the pulse duration and the average power during the pulse, the pulse energy may be determined in order to control the system. This may be used, for example, during micropulse operation at peak power levels of between 200 milliwatts (200 mW) and 1 watt (1 W), or at other suitable peak power levels.

In some embodiments, the power adjustments may be made while the laser is operating but not being used therapeutically. For example, the system 50 may include one or more shutters in the line of laser output, downstream from the sensor 22 and/or 28. The shutter can block the laser output, such that it does not exit the system (e.g., does not reach the retina of the patient). With the shutter closed, the system 50 may be used to monitor and adjust the laser power to the desired level as described above, prior to opening the shutter for therapeutic use of the laser.

As would be understood by persons of ordinary skill in the art, systems and methods as disclosed herein have advantages over prior systems and methods. For example, in some prior systems and methods, laser output has been determined based upon the electrical signal that is used to drive the laser, which can have significant drawbacks when the visible output of the laser does not directly follow the supplied current. Systems and methods as described herein can measure the laser output directly using one or more sensors that detect that output, providing more accurate information as compared to systems and methods that determine laser output based upon the electrical input.

In other prior systems and methods, laser output has been determined by using a sensor that continuously samples laser output, which can require very high sample rates and can place high demands on processor activity. Systems and methods as described herein provide accurate synchronization of the data collection to the optical pulse. Systems and methods as described herein are configured to directly measure the time when the laser output turns on, or on and off, allowing the duty cycle of the laser to be continuously monitored with great accuracy, in turn allowing the systems and methods to sample the average power at several selected points during each pulse in a plurality of pulses. From this sampling, the total energy contained in each pulse in a plurality of pulses can be determined. Systems and methods as described herein that measure the laser output at selected sample times during each pulse in a plurality of pulses, as opposed to continuously, provide accurate information while placing far less demand on processing activity.

In addition, with fast pulsing lasers with very short laser pulses, for example sub-millisecond pulses that may be on the order or microseconds, a system that continuously monitors laser output would place very burdensome demands on processing activity. Systems and methods as described herein that measure the laser output at selected sample times during a pulse allow monitoring of fast pulsing lasers with a significantly reduced sample rate and a corresponding significant reduction in processing requirements.

Systems and methods as described herein can work at different power levels and can work even if the pulse shape changes over the time. The sample information can be used in a feedback loop to maintain the pulse energy within a required tolerance for safe operation or within a desired range.

Depending on the application, as would be understood by persons of ordinary skill in the art in view of this disclosure, components as described herein may be implemented as hardware, software, firmware, and/or a combination. Communication paths may be by physical connections or wireless connections. As an example, the analog to digital converter may exist on a microcontroller that implements the controller or may be implemented as a stand-alone integrated circuit or other component. As another example, the edge detector may exist on the microcontroller that implements the controller or may be a part of programmable logic that implements the controller or may be a stand-alone component.

Persons of ordinary skill in the art will appreciate that the implementations encompassed by the disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. A system for measuring pulsed laser output, the system comprising:
    a laser configured to emit output in pulses;
    at least one sensor positioned to sense output from the laser and configured to convert that output into electrical signals;
    an edge detector configured to receive electrical signals from the at least one sensor and to detect from those electrical signals at least leading edges and trailing edges of a plurality of pulses from the laser;
    an analog to digital converter configured to receive electrical signals from the at least one sensor and to convert those electrical signals into digital signals indicative of laser power output; and
    a controller;
    wherein, based on the detection by the edge detector of at least the detected leading edges of the plurality of pulses from the laser, the controller is configured to obtain from the analog to digital converter a plurality of samples of laser power output between a detected leading edge and a detected trailing edge of each of the plurality of pulses from the laser; and
    wherein, based on the detection by the edge detector of the detected trailing edges, the controller is configured to sample laser power output between pulses from the laser at a reduced sample rate as compared to a sample rate of laser power output between the detected leading edges and the detected trailing edges.

2. The system of claim 1, wherein, based on the detection by the edge detector of the detected leading edges and the detected trailing edges of the plurality of pulses from the laser, the controller is configured to obtain from the analog to digital converter the plurality of samples of laser power output during each of the plurality of pulses from the laser.

3. The system of claim 1, wherein the controller is configured to refrain from sampling laser power output between pulses from the laser.

4. The system of claim 1, wherein the system is configured to use the plurality of samples of laser power output during each of the plurality of pulses from the laser in a feedback loop to automatically adjust laser power to a desired level.

5. The system of claim 1, wherein the laser is configured to emit output in pulses ranging in duration from 1 microsecond to 100 microseconds.

6. The system of claim 1, wherein the laser is an intracavity doubled diode pumped solid state laser.

7. The system of claim 1, wherein the at least one sensor positioned to sense output from the laser and configured to convert that output into electrical signals comprises a first sensor configured to send electrical signals at least to the edge detector and a second sensor configured to send electrical signals at least to the analog to digital converter.

8. The system of claim 1, wherein the at least one sensor positioned to sense output from the laser and configured to convert that output into electrical signals comprises a single sensor configured to send electrical signals to the edge detector and to the analog to digital converter.

9. The system of claim 1, wherein the at least one sensor positioned to sense output from the laser and configured to convert that output into electrical signals comprises at least one photodiode sensor.

10. The system of claim 1, wherein the system further comprises a driver that is configured to drive the laser and that is configured to be controlled by the controller.

11. The system of claim 1, wherein the system further comprises a sync timer configured to enable keeping track of time between one or more components of the system.

12. A system for measuring pulsed laser output, the system comprising:
    a laser configured to emit output in pulses;
    at least one sensor positioned to sense output from the laser and configured to convert that output into electrical signals;
    an edge detector configured to receive electrical signals from the at least one sensor and to detect from those electrical signals leading edges and trailing edges of a plurality of pulses from the laser;

an analog to digital converter configured to receive electrical signals from the at least one sensor and to convert those electrical signals into digital signals indicative of laser power output; and a controller;

wherein, based on the detection by the edge detector of the detected leading edges and the detected trailing edges of the plurality of pulses from the laser, the controller is configured to obtain from the analog to digital converter a plurality of samples of laser power output during each pulse of the plurality of pulses from the laser;

wherein, based on the detection by the edge detector of the detected trailing edges, the controller is configured to sample laser power output between pulses from the laser at a reduced sample rate as compared to a sample rate of laser power output between the detected leading edges and the detected trailing edges; and wherein the system is configured to use the plurality of samples of laser power output between a detected leading edge and a detected trailing edge of each pulse of the plurality of pulses from the laser in a feedback loop to automatically adjust laser power to a desired level.

13. A method of measuring pulsed laser output, the method comprising:

operating a laser to emit output in pulses;

sensing the output from the laser and converting that output to electrical signals;

detecting from the electrical signals leading edges and trailing edges of a plurality of pulses from the laser;

based at least on the detection of the detected leading edges of the plurality of pulses, obtaining a plurality of samples of laser power output between a detected leading edge and a detected trailing edge of each of the plurality of pulses from the laser; and based at least on the detection of the detected trailing edges of the plurality of pulses, reducing sample rate between pulses from the laser as compared to a sample rate of the laser between the detected leading edge and the detected trailing edge.

14. The method of claim 13, wherein the step of obtaining the plurality of samples of laser power output during each of the plurality of pulses from the laser is performed based the detection of the detected leading edges and the detected trailing edges of the plurality of pulses.

15. The method of claim 13, wherein the step of obtaining a plurality of samples of laser power output during each of the plurality of pulses from the laser is performed at a first sample rate, and further comprising obtaining one or more samples of laser power output between pulses from the laser at a second sample rate, wherein the second sample rate is lower than the first sample rate.

16. The method of claim 13, further comprising refraining from sampling laser power output between pulses from the laser.

17. The method of claim 13, further comprising using the plurality of samples of laser power output during each of the plurality of pulses from the laser in a feedback loop to automatically adjust laser power to a desired level.

* * * * *